United States Patent [19]

Duffin, Jr.

[11] Patent Number: 5,243,978
[45] Date of Patent: Sep. 14, 1993

[54] METHOD AND APPARATUS FOR WIDE AREA ANTITACHYCARDIA PACING

[75] Inventor: Edwin G. Duffin, Jr., New Brighton, Minn.

[73] Assignee: Medtronic, Inc., Minneapolis, Minn.

[21] Appl. No.: 772,720

[22] Filed: Oct. 7, 1991

[51] Int. Cl.$^5$ .......................................... A61N 1/365
[52] U.S. Cl. ..................................................... 607/11
[58] Field of Search .......... 128/419 D, 419 PG, 784, 128/785, 786, 419 P

[56] References Cited

U.S. PATENT DOCUMENTS

| | | |
|---|---|---|
| 3,937,226 | 2/1976 | Funke .......................... 128/419 PG |
| 4,340,062 | 7/1982 | Thompson ................... 128/419 PG |
| 4,406,286 | 9/1983 | Stein ............................. 128/419 PG |
| 4,548,209 | 10/1985 | Wielders ....................... 128/419 D |
| 4,595,009 | 6/1986 | Leinders ....................... 128/419 D |
| 4,693,253 | 9/1987 | Adams .......................... 128/419 D |
| 4,790,317 | 12/1988 | Davies .......................... 128/419 PG |
| 4,821,723 | 4/1989 | Baker ............................ 128/419 D |
| 4,895,151 | 1/1990 | Grevis et al. ................. 128/419 PG |
| 4,953,551 | 9/1990 | Mehra et al. ................. 128/419 PG |
| 4,971,070 | 11/1990 | Holleman ..................... 128/784 |
| 4,989,602 | 2/1991 | Sholder et al. .............. 128/419 PG |
| 5,033,467 | 7/1992 | Bocchi et al. ................ 128/419 PG |
| 5,109,842 | 5/1992 | Adinolfi ........................ 128/784 |

Primary Examiner—William E. Kamm
Assistant Examiner—George Manuel
Attorney, Agent, or Firm—Reed A. Duthler; Harold R. Patton

[57] ABSTRACT

A pacemaker system adapted to delivery pacing pulses in the presence of tachycardia or bradycardia. The pacing pulses are delivered via large surface area electrodes of the type normally used to accomplish defibrillation or cardioversion. Delivery of pacing pulses using the large surface area electrodes results in a more simultaneous depolarization of the heart tissue and is believed beneficial to improve hemodynamic efficiency of paced heart beats and in terminating detected tachyarrhythmias.

8 Claims, 2 Drawing Sheets

METHOD AND APPARATUS FOR WIDE AREA ANTITACHYCARDIA PACING

BACKGROUND OF THE INVENTION

This invention relates generally to implantable stimulators and, more specifically, to implantable pacemakers, cardioverters and defibrillators.

Over the years, numerous methods have been proposed for pacing the heart in an attempt to interrupt tachycardias. These include such pacing modalities as overdrive pacing, burst pacing, autodecremental overdrive pacing, and others. These pacing modalities have been formulated to interrupt conduction on aberrant cardiac conduction paths, which may lead to sustained tachycardias in one or more chambers of the heart.

In recent years, attention has been focused on the use of pacing pulses delivered using standard cardiac pacing electrode systems located in the atrium and/or ventricle. Typical electrode systems for delivery of antitachycardia pacing pulses have included: unipolar systems, utilizing an electrode located on or in one chamber of the heart and a remote electrode; bipolar systems, employing two electrodes located on or in a chamber of the heart; and integrated bipolar systems, employing a small surface area pacing electrode located on or in a chamber of the heart in conjunction with a large surface area electrode located on the heart, typically a defibrillation electrode. Each of these approaches to pacing assumes that the active pacing electrode is a single small surface area electrode, and that propagation of the depolarization wavefront within the heart begins adjacent to the pacing electrode, and then propagates throughout the heart from the tissue adjacent the pacing electrode.

A commonly held principle of antitachycardia pacing is that paced termination of a tachycardia is facilitated if the stimulating electrode is positioned close to the reentrant circuit. This condition is often difficult to achieve since electrodes cannot be readily placed in many regions of the heart, nor is it always evident where the preferred placement lies.

In the past, it was proposed that tachycardias could be interrupted by the use of multi-site cardiac pacing. One early example of multi-site cardiac pacing to terminate or prevent tachyarrhythmia is disclosed in U.S. Pat. No. 3,937,226 issued to Funke. In this device, a number of small surface area pacing electrodes are provided, each coupled to a separate output circuit and amplifier. The disclosed device is equivalent to five or more separate cardiac pacemaker output circuits of conventional design, all adapted to be triggered to pace simultaneously at various locations around the heart. It is hypothesized that by stimulating simultaneously at locations spread around the heart, synchronous with a sensed QRS complex, arrhythmias could be prevented by producing a more nearly simultaneous depolarization of cardiac tissues.

SUMMARY OF THE INVENTION

The present invention provides a method and apparatus for cardiac pacing which attempts to: minimize the occurrence of tachyarrhythmias by causing more synchronous depolarization of a large mass of cardiac tissue; enhance the efficacy of antitachycardia pacing by increasing the ability to depolarize tissue close to the focus of a tachyarrhythmia; and enhance the hemodynamic efficacy of paced cardiac depolarizations by causing a more synchronous contraction of a larger number of cardiac fibers. Rather than employ multiple output circuits and electrode sets, the present invention employs two or more large surface area electrodes, located on or in the heart. In its most likely commercial implementation, it is believed that these large surface area electrodes will constitute defibrillation electrodes, and that the invention will be embodied as part of an implantable pacemaker/cardioverter/defibrillator system.

It has been determined experimentally that standard voltage pacing pulses (e.g., 5 volts), delivered to existing epicardial defibrillation electrodes will reliably pace the heart. It has also been determined that the QRS complexes resulting from pacing the heart in this fashion are substantially narrower in width than QRS complexes resulting from bipolar cardiac pacing using traditional, small surface area pacing electrodes.

In order to practice the invention, the pacing pulse generator must be designed to provide an output voltage adjustable up to at least 5 volts, and preferably 10 volts, into a low resistance electrode system having an impedance of 20–100 ohms. This can be readily accomplished by employing an output capacitor of 100 to 200 $\mu$farads (with an appropriately modified charging circuit), instead of output capacitors in the range of 10–20 $\mu$farads, as is typically employed in cardiac pulse generators. This is necessary because the low impedance of typical available epicardial defibrillation electrode systems requires a higher current to maintain the voltage of the pacing pulse.

It is proposed that the present invention may best be practiced in the context of an implantable pacemaker/cardioverter/defibrillator of the type employing large surface area epicardial and/or endocardial electrodes. In this case, the invention is preferably embodied by including a pacemaker output circuit, adapted to pace into a load of 20 to 100 ohms as described above, combined with electronic switches to allow either high voltage pulses from the cardioverter/defibrillator output circuit within the device or pacing pulses from the low impedance pacing output circuit to be applied to the large surface area electrodes. The pacing circuit preferably shares the large capacitor typically used by the cardioverter/defibrillator output circuit, as such capacitors typically occupy considerable volume. It is proposed that the tachycardia detection methodologies used in presently existing devices may be retained, and that the use of the large surface area electrodes in conjunction with the additional pacing pulse generator simply be added as an additional available therapy.

Delivery of pacing pulses to the large surface area defibrillation electrodes may be performed using any of the known antitachycardia pacing methodologies, including one or more precisely timed premature stimuli, overdrive pacing, fixed rate or adaptive rate burst pacing, autodecremental overdrive pacing, and R-wave coupled pacing, wherein one or more pacing pulses are delivered synchronized to a sensed cardiac depolarization. As in the case of the existing devices, it is anticipated that the physician will tailor the pacing pulse methodology to the particular patient, based upon the results of the electrophysiological work-up proceeding implant of the device.

For antibradycardia pacing the physician can program the system to pace using a small capacitor (e.g. 10–20 $\mu$farads) of the type used in conventional pacemakers to conserve battery life. However, when the patient demonstrates a need for improved hemodynamic efficiency, or if arrhythmia prevention capability is required, antibradycardia pacing can also be accomplished utilizing the larger output capacitor and electrodes.

DETAILED DESCRIPTION OF THE PREFERRED EMBODIMENT

Figure 1:
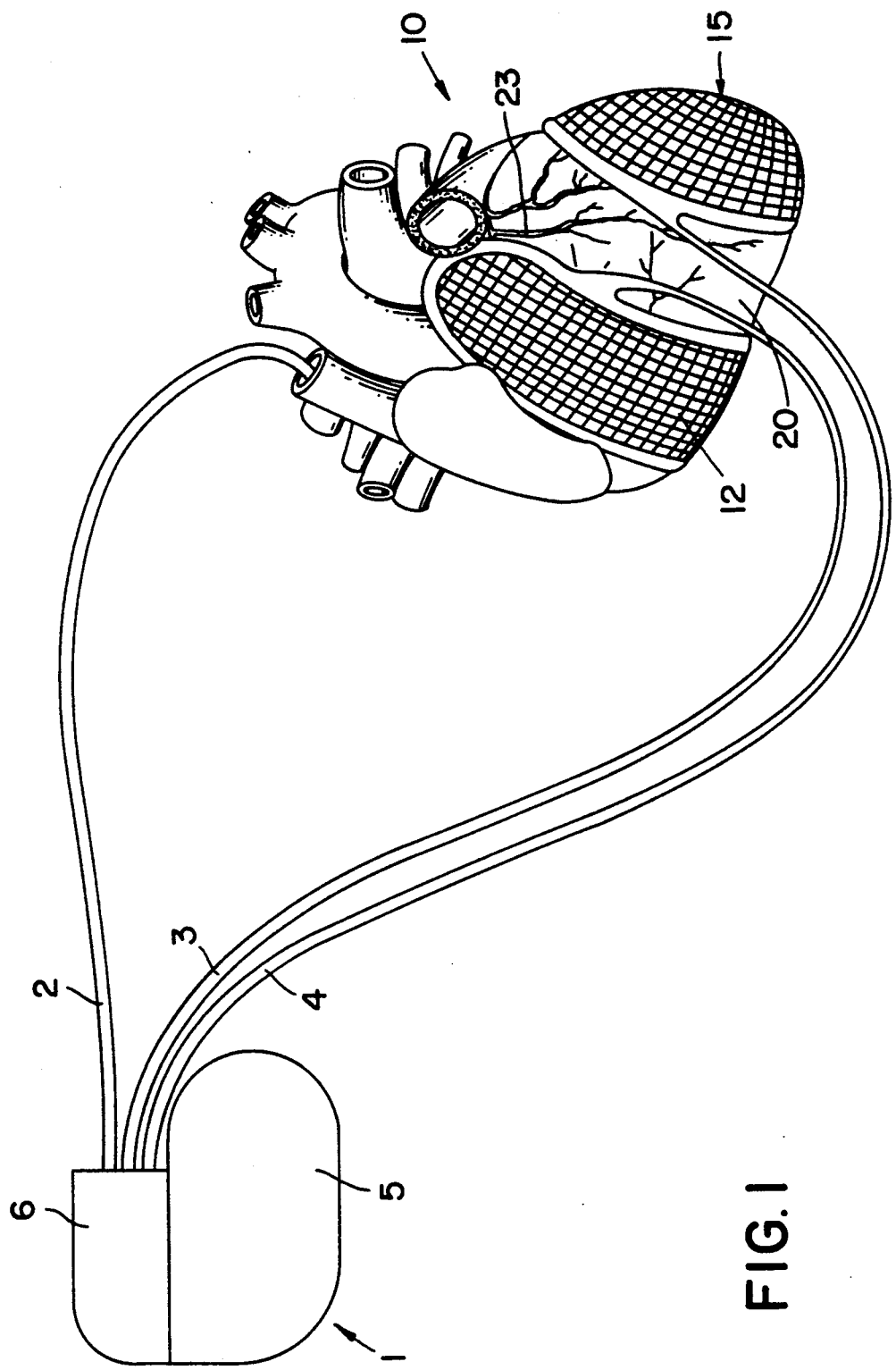
FIG. 1 is a plan view of an implantable pacemaker/cardioverter/defibrillator and associated lead system, illustrating the location of the leads and electrodes in relation to a human heart.

FIG. 1 is a plan view of an implantable pacemaker/cardioverter/defibrillator, 1 and its associated lead system, in conjunction with a human heart 10. As illustrated, the device includes a right ventricular lead 2, and two epicardial electrode leads 3, and 4. Leads 3 and 4 are provided with large surface area electrodes 12 and 15, respectively, adapted to located on the heart. The illustrated electrode system is adapted from the disclosure of U.S. Pat. No. 4,821,723 issued to Baker, et al. However, it is believed that any pair of large surface area defibrillation electrodes may be usefully employed to practice the present invention. For example, electrodes as disclosed in U.S. Pat. No. 4,971,070 issued to Holleman, et al., incorporated herein by reference in its entirety, may also be used. Electrodes of this type have in fact been tested at the request of the inventor of the present application and it has been determined that, in conjunction with a cardiac pacemaker modified to pace into a 50 ohm load, reliable cardiac pacing may be accomplished with an output of 5 volts. In any case, it is desired that the epicardial electrodes have a relatively large surface area, and be disbursed over a substantial portion of the epicardium of the heart. Electrodes having electrode surfaces connected in common and extending over or dispersed over areas of approximately 30 to 80 square centimeters each are believed to be particularly appropriate for use in conjunction with the present invention. Alternatively, multiple electrode leads connected in common may be substituted for individual large surface area electrodes, if desired.

The right ventricular lead 2, may be a conventional bipolar ventricular pacing lead, serving to perform normal cardiac pacing functions and to sense ventricular depolarizations. Alternatively, lead 2 may be a unipolar lead, and cardiac pacing and/or sensing of ventricular depolarizations may be accomplished between an electrode located on lead 2 and a patch electrode located on the epicardium or an electrode located on the housing of the device 1.

For purposes of the present invention, it is envisioned that the electrodes located on the right ventricular lead 2, or a corresponding epicardial electrode or electrodes will be used for routine VVI pacing in the presence of bradycardia, for sensor based rate responsive cardiac pacing, if the device is so equipped, and for antitachycardia pacing, if the physician so desires. However, when hemodynamic augmentation is required, or when antitachycardia pacing is desired, either for prevention or termination of tachyarrhythmias, the system can be programmed to deliver pacing level therapy using the large surface area electrodes 12 and 15.

Figure 2:
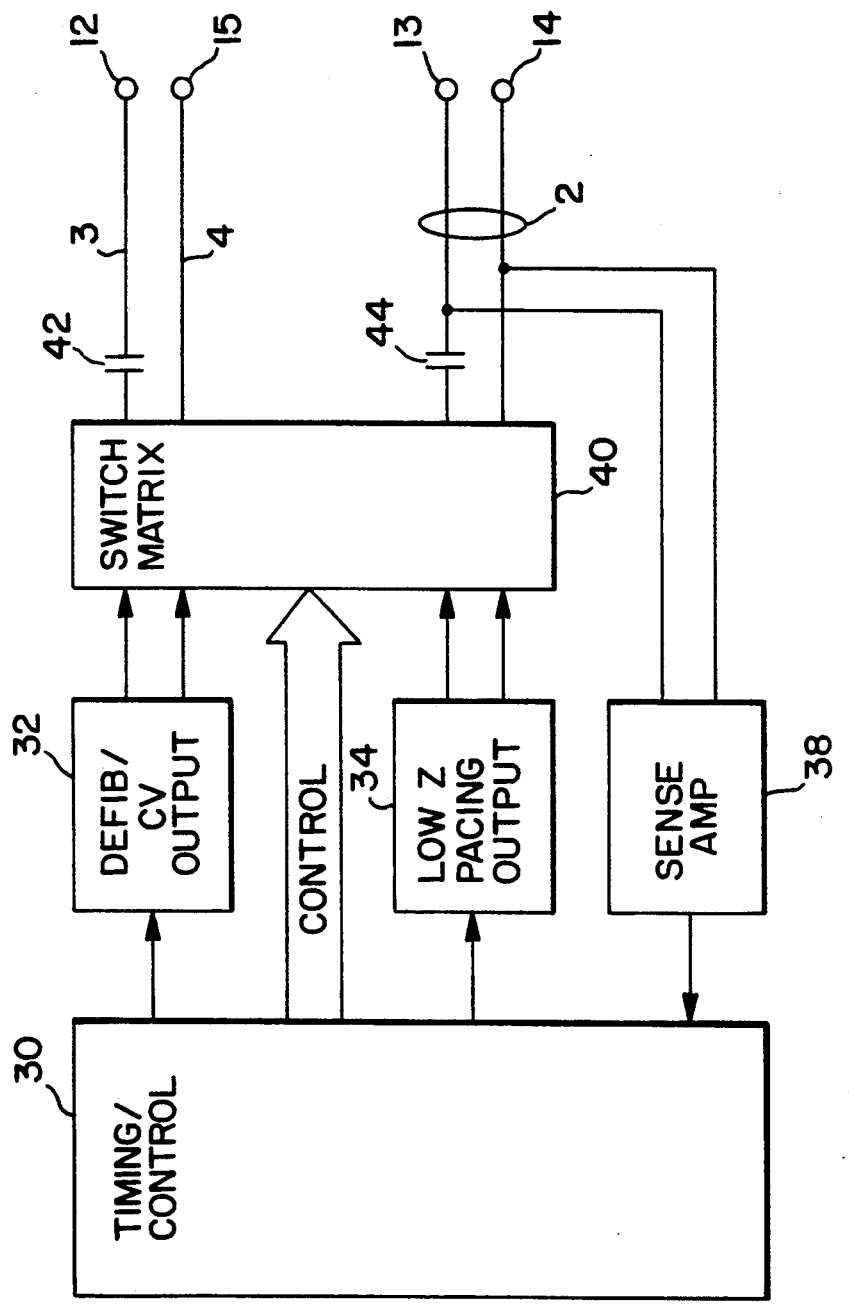
FIG. 2 is block diagram of a prior art implantable pacemaker/cardioverter/defibrillator, to which a low impedance pacing output stage and an associated switch matrix, allowing selective delivery of antibradycardia pacing pulses and antitachycardia pacing pulses to the cardioversion/defibrillation electrodes has been added.

FIG. 2 is a block diagram illustrating the major functional components of the implanted pacemaker/cardioverter/defibrillator 1 illustrated in FIG. 1. Timing and control functions are accomplished by timing and control logic 30, which is preferably a microprocessor based system, corresponding to those used in presently available pacemaker/cardioverter/defibrillator systems. The basic function and operation of the timing and control logic 30 may correspond to the microprocessor controlled systems disclosed in U.S. Pat. No. 4,407,288 issued to Langer et al. on Oct. 4, 1983, U.S. Pat. No. 5,022,395, issued to Russie on Jun. 11, 1991, U.S. Pat. No. 4,958,632 issued to Duggan on Sep. 25, 1990 or in U.S. Pat. No. 4,830,006 issued to Haluska et al. on May 16, 1989, all of which are incorporated herein by reference in their entireties. For purposes of the present invention, it is only important to understand that the timing/control circuitry detects the occurrence of bradycardia and/or tachycardia and in response thereto controls the delivery of the various pacing, cardioversion and defibrillation therapies available. In the context of the present invention, it is envisioned that the high voltage cardioversion and defibrillation therapies may simply correspond to those available in the prior art, and the present invention is not directed toward improving or adapting these therapies.

The high voltage defibrillation/cardioversion pulses are provided by the Defib/CV output circuit 32, under control of timing/control circuitry 30. Typically, this circuit will be capable of charging and discharging capacitor 42 to produce output pulses in excess of 300 volts into a 50 ohm load. In any case, the circuit 32 should be capable of delivering pulses in excess of 0.2 joules. Examples of appropriate circuitry for accomplishing the generation of cardioversion and defibrillation pulses are set forth in U.S. Pat. No. 4,595,009 issued to Lein Jun. 17, 1986, U.S. Pat. No. 4,548,209 issued to Wielders on Oct. 22, 1985, U.S. Pat. No. 4,693,253 issued to Adams on Sep. 15, 1987, U.S. Pat. No. 4,935,551 issued to Mehra et al. on Sep. 4, 1990, or U.S. pat. application Ser. No. 07/612,758, filed Nov. 14, 1990 by Keimel, for an "Apparatus for Delivering Single and Multiple Cardioversion Pulses", all of which are also incorporated herein by reference in their entireties. For purposes of the present invention, it is believed that any prior art defibrillation/cardioversion output circuit may be usefully employed.

The sensing circuit 38 is a conventional cardiac sensing circuit and may be equivalent to any prior art cardiac sensing circuits employed in previous devices. For example, the sensing circuit may correspond to the circuit disclosed in U.S. Pat. No. 4,266,551 issued to Stein on May 21, 1981, U.S. Pat. No. 4,275,737 issued to Thompson et al, U.S. Pat. No. 4,649,931 issued to Beck on Mar. 17, 1987 or in U.S. pat. application Ser. No. 07/612,760 filed Nov. 14, 1990 by Keimel et al. for an "Apparatus for Monitoring Electrical Physiological Signals", all of which are incorporated herein by reference in their entireties.

The low impedance pacing output circuitry 34 may correspond generally to the output circuitry illustrated in U.S. Pat. No. 4,406,286 issued to Stein on Sep. 27, 1983 or U.S. Pat. No. 4,340,062 issued to Thompson et al. on Jul. 20, 1982, both of which are also incorporated herein by reference in their entireties, with the exception that the circuit must be slightly modified to pace into somewhat lower impedances than typical implantable pacers, e.g., 50 ohms or less. This will be accomplished by using a larger value output capacitor, for example in the range of 100 μfarads, and by increasing the current available for recharging the larger output capacitor. These modifications are believed to be well within the ability of one skilled in the art, and are therefore not discussed in detail. For purposes of the present invention any circuit capable of generating pacing pulses at an amplitude of 5 to 10 volts, with a pulse width of about 0.1 millisecond to about 1 millisecond should be sufficient. As disclosed in FIG. 2, the cardioversion output capacitor 42 may be shared between the cardioversion and pacing output circuits for delivery of pulses to the large surface area electrodes 12 and 15.

The sense amp circuitry 38 is coupled to right ventricular lead 2, and to a pair of electrodes 13 and 14, located adjacent to distal end of the lead 2. Alternatively, the sense amp circuit 38 may be coupled to only one of the electrodes 13 and 14, and may sense between that electrode and the conductive housing of the implantable device or one of the large surface electrodes.

As discussed above, selection between bradycardia pacing and antitachycardia pacing and selection between antitachycardia pacing, cardioversion, and defibrillation therapies may correspond to any prior art implantable pacemaker/cardioverter/defibrillator, with the added feature that, if programmed by the physician to do so, the device is capable of selectively coupling the low impedance pacing output stage 34 to the large surface area defibrillation electrodes 12 and 15, and delivering antibradycardia and antitachycardia pacing pulses thereto, under control of the timing/control circuitry 30.

Switch matrix 40 shown in block format is simply a collection of one or more FET and/or SCR switches activated under control of timing/control circuitry 30 to selectively couple either the defibrillation/cardioversion output circuity 32 or the low impedance pacing output circuity 34 to the high value capacitor 42 and the large surface area electrodes 12 and 15. Examples of switch matrixes of controlled electrical switches used to selectively couple defibrillation electrodes to output circuity may be found in the above-cited Mehra et al. patent, the above-cited Keimel et al. application or U.S. Pat. No. 4,800,883 issued to Winstrom on Jan. 31, 1989, incorporated herein by reference in its entirety. It is believed that any of these systems may be adapted for switching the connection of electrodes 12 and 15 between the high voltage output circuitry 32 and the low impedance pacing output circuity 34. It is also believed that construction of such switch matrixes is well within the ability of one of skill in the art, given the teaching in the cited references.

Switch matrix 40 preferably also selectively couples the pacing circuitry 34 to either pacing output capacitor 44 and small surface area electrodes 13 and 14 or to capacitor 42 and electrodes 12 and 15. Thus, antitachycardia and antibradycardia pacing may be performed using either the large surface are electrodes or using conventional pacing electrodes 13 and 14.

As noted above, testing undertaken at the request of the inventor of the present application has revealed that cardiac pacing employing large surface area epicardial electrodes results in a substantial narrowing of the QRS complex as compared to standard paced beats. This in turn is believed to indicate a more simultaneous depolarization of cardiac tissue in response to the delivery of the pacing pulse, which in turn should provide for less dispersion of the refractory periods associated with various portions of the heart tissue. Moreover, the dispersion of the pacing electrode surface over a substantial area of the heart increases the likelihood that tissue at or adjacent to the re-entrant conduction path will be depolarized by the delivered pacing pulse. As such, tachycardia which is due to re-entrant conduction pathways should be prevented and/or terminated by pacing pulses delivered using the large surface electrode system.

While the large surface area electrode system does require a pacing pulse generator with higher output current capabilities, the overall energy delivered with each such pacing pulse is not substantial as compared to the delivery of a cardioversion or defibrillation pulse. It is believed that in most cases, pacing pulses of 5 millijoules or less should be sufficient to reliably pace the heart. In general, it is believed that pacing using large surface area epicardial electrodes to achieve a more simultaneous depolarization of heart tissue can be accomplished readily using individual pulses having energy levels of less than 1 millijoule, and typically with energies less than 0.5 millijoule.

For example, delivery of a 5 volt pacing pulse into a 50 ohm load, using a 0.5 millisecond pulse width (the parameters tested) results in the expenditure of only 0.25 millijoules per pulse. While this is a substantial increase over standard pacing pulses, it should not pose a significant problem for occasionally activated antitachycardia or antibradycardia pacing pulse regimens. Slightly higher energies may be required for transvenous, large surface area electrode systems.

While the above disclosed implementation employs large surface area electrodes located on the ventricles, it is believed that the present invention may also be applicable to antitachycardia and antibradycardia pacing of the atria, and/or pacing regimens delivered to both the atria and ventricles. In addition, while the disclosed embodiment is illustrated as a microprocessor based apparatus, similar to presently marketed devices, it is also within the scope of the invention to employ substantially simpler devices to deliver pacing pulses via the large surface area electrodes. For example, a simple device which detects the occurrence of heart rates in excess of a predetermined threshold and thereafter generates cardiac pacing pulses for application via the large surface electrodes, synchronized to sensed R waves, may provide a simple, useful implementation of the present invention, even in the absence of an associated cardioverter and/or defibrillator. As such, the above disclosure should be taken as exemplary, rather than limiting with regard to the scope of the following claims. In the claims which follow, the term "cardioversion" is employed. For purposes of understanding the claims, this term should be interpreted to broadly include electrical pulse therapies for converting tachycardias including fibrillation to normal rhythm using one or more high voltage pulses rather than using pacing pulses.

In conjunction with the above disclosure, I claim:
1. An antitachycardia pacemaker, comprising:
   first and second electrode means for delivering energy to a patient's heart, adapted to be mounted to a patient's heart, said electrode means each having electrode surfaces extending or dispersed over an area of at least approximately 30 square centimeters;

means for sensing the rhythm of said patient's heart and for determining the presence of a tachyarrhythmia; and pulse generator means responsive to the detection of a tachyarrhythmia in said patient's heart for providing cardiac pacing pulses to said first and second electrode means.

2. An antitachycardia pacemaker according to claim 1 wherein said electrode means comprise epicardial electrode leads.

3. A pacemaker according to claim 1 or claim 2 wherein said pulse generator means comprises means for generating pulses of 5 millijoules or less for application to said patient's heart to pace said patient's heart.

4. A cardioverter/antitachycardia pacemaker comprising:

first and second cardioversion electrodes, adapted to be mounted to a patient's heart;

means for sensing the rhythm of said patient's heart and for detecting the occurrence of a tachyarrhythmia;

cardioverter pulse generator means responsive to detection of tachyarrhythmia by said sensing means for generating cardioversion pulses for application to said patient's heart;

pacing pulse generator means for generating cardiac pacing pulses for application to said patient's heart; and means for coupling said pacing pulse generator means and said cardioversion pulse generator means to said cardioversion electrodes.

5. A cardioverter/defibrillator according to claim 4, wherein said first and second electrode means are epicardial electrodes, each having electrode surfaces extending or dispersed over at least 30 square centimeters.

6. A cardioverter/pacemaker according to claim 4 or claim 5 wherein said pacing pulse generator comprises means for generating pacing pulses of 5 millijoules or less for application to said first and second large surface area electrodes.

7. A cardioverter/pacemaker according to claim 6, wherein said cardioversion pulse generator comprises means for generating cardioversion pulses of at least 0.2 joules, for application to said electrode means.

8. A pacemaker comprising:

first and second electrode means for delivering cardiac pacing pulses to a patient's heart, each electrode means having electrode surfaces connected in common and extending or dispersed over an area of at least about 30 square centimeters and adapted to be mounted to a patient's heart; and pacing pulse generator means for generating cardiac pacing pulses for application to said first and second electrode means.

* * * * *